(12) United States Patent
DiSilvestro (10) Patent No.: US 8,734,454 B2
(45) Date of Patent: *May 27, 2014

(54) METHOD AND APPARATUS FOR USE IN BALANCING LIGAMENTS OF A KNEE

(71) Applicant: DePuy Synthes Products, Inc., Raynham, MA (US)

(72) Inventor: Mark R. DiSilvestro, Columbia City, IN (US)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/774,631

(22) Filed: Feb. 22, 2013

(65) Prior Publication Data

US 2013/0165940 A1 Jun. 27, 2013

Related U.S. Application Data

(60) Continuation of application No. 12/572,385, filed on Oct. 2, 2009, now Pat. No. 8,394,104, and a division of application No. 11/094,956, filed on Mar. 31, 2005, now Pat. No. 7,615,055.

(51) Int. Cl.
*A61B 17/58* (2006.01)

(52) U.S. Cl.
USPC ............................................. 606/88; 606/90

(58) Field of Classification Search
USPC ................................ 606/88, 90; 600/594–595
See application file for complete search history.

(56) References Cited

U.S. PATENT DOCUMENTS

| | | | |
|---|---|---|---|
| 4,501,266 A | 2/1985 | McDaniel | |
| 4,899,761 A | 2/1990 | Brown et al. | |
| 4,973,331 A | 11/1990 | Pursley et al. | |
| 5,082,003 A | 1/1992 | Lamb et al. | |
| 5,213,112 A | 5/1993 | Niwa et al. | |
| 5,329,933 A | 7/1994 | Graf | |
| 5,540,696 A | 7/1996 | Booth et al. | |
| 5,688,280 A | 11/1997 | Booth et al. | |

(Continued)

FOREIGN PATENT DOCUMENTS

| | | |
|---|---|---|
| DE | 10335410 | 2/2005 |
| EP | 0720834 | 6/1999 |

(Continued)

OTHER PUBLICATIONS

European Search Report for European Patent Application No. 06251808.9-2310, Jul. 14, 2006, 3 pgs.

*Primary Examiner* — Nicholas Woodall
(74) *Attorney, Agent, or Firm* — Barnes & Thornburg LLP (57) ABSTRACT

An orthopaedic surgical instrument includes an orthopaedic distraction device sized to be positioned between a distal end of a patient's femur and a proximal end of the patient's tibia and configured to apply force between the patient's femur and the patient's tibia. The orthopaedic surgical instrument also includes a user-operated control device operable to actuate the orthopaedic distraction device to apply force between the patient's femur and the patient's tibia. In actuating the orthopaedic distraction device, a rotary input of the user-operated control device that is coupled to the orthopaedic distraction device may be used. The orthopaedic surgical instrument also includes a display positioned on an outer surface of the orthopaedic distraction device and a circuit configured to control the display. The display is configured to provide visual feedback indicative of force applied by the distraction device.

14 Claims, 4 Drawing Sheets

(56) References Cited

U.S. PATENT DOCUMENTS

| | | | |
|---|---|---|---|
| 6,022,377 | A | 2/2000 | Nuelle et al. |
| 6,648,896 | B2 | 11/2003 | Overes et al. |
| 6,758,850 | B2 | 7/2004 | Smith et al. |
| 7,153,281 | B2 | 12/2006 | Holmes |
| 7,578,821 | B2 * | 8/2009 | Fisher et al. .................... 606/88 |
| 2002/0156480 | A1 | 10/2002 | Overes et al. |
| 2003/0144669 | A1 | 7/2003 | Robinson |
| 2003/0153978 | A1 | 8/2003 | Whiteside |
| 2003/0236472 | A1 | 12/2003 | Van Hoeck et al. |
| 2004/0039254 | A1 | 2/2004 | Stivoric et al. |
| 2004/0097951 | A1 | 5/2004 | Steffensmeier |
| 2005/0038442 | A1 | 2/2005 | Freeman |
| 2005/0234448 | A1 | 10/2005 | McCarthy |
| 2010/0249790 | A1 | 9/2010 | Roche |
| 2010/0249791 | A1 | 9/2010 | Roche |

FOREIGN PATENT DOCUMENTS

| | | |
|---|---|---|
| EP | 1348382 | 10/2003 |
| WO | PCT/99/35972 | 7/1999 |
| WO | PCT/2003/065949 | 8/2003 |
| WO | PCT/2004/008988 | 1/2004 |
| WO | PCT/2005/023120 | 3/2005 |
| WO | PCT/2005/089681 | 9/2005 |

* cited by examiner

METHOD AND APPARATUS FOR USE IN BALANCING LIGAMENTS OF A KNEE

This application claims priority under 35 U.S.C. §120 to U.S. patent application Ser. No. 12/572,385, which was filed on Oct. 2, 2009 with projected U.S. Pat. No. 8,394,104, and which is a divisional application of U.S. patent application Ser. No. 11/094,956, which was filed on Mar. 31, 2005 and issued as U.S. Pat. No. 7,615,055. Each of those application is incorporated herein by reference.

TECHNICAL FIELD

The present disclosure relates generally to methods and apparatus for use in the performance of orthopaedic procedures such as knee replacement procedures.

BACKGROUND

In some orthopaedic surgical procedures, such as a total knee replacement procedure, ligament balancing devices (commonly known as ligament balancers) may be used to balance the surrounding soft tissue (i.e., ligaments) of a patient's joint. For example, in a total knee replacement procedure, ligament balancing may be performed to ensure a generally rectangular shaped extension gap and a generally rectangular shaped flexion gap at a predetermined joint force value between the patient's natural or prosthetic proximal tibia and the patient's natural or prosthetic distal femur. To do so, a ligament balancer may be used to measure the medial and lateral joint forces and the medial and lateral gap distances when the patient's leg is in extension (i.e., the patient's tibia is positioned at about 0 degrees relative to the patient's femur) and in flexion (i.e., the patient's tibia is positioned at about 90 degrees relative to the patient's femur). In either extension or flexion, if the medial and lateral gap distances are not approximately equal (i.e., do not form a generally rectangular shaped joint gap) at the predetermined joint force value, ligament release may be performed to equalize the medial and/or lateral gap distances. A typical ligament balancer includes manually operated mechanical mechanisms, such as springs, to determine the joint force and to adjust the extension/flexion gap distance.

SUMMARY

According to one aspect, an apparatus for use in performing an orthopaedic surgical procedure on a patient is disclosed. The apparatus may include one or more femoral paddles configured to contact a natural or prosthetic distal femur of a patient. The apparatus may also include one or more tibial paddles configured to contact a natural or prosthetic proximal tibia of the patient. At least one of the femoral paddle and/or the tibial paddle is movable away from the other. The apparatus may include a force sensor operatively coupled to the femoral paddle and/or the tibial paddle. The force sensor generates an output signal that is indicative of the magnitude of the force applied to the respective paddle. The apparatus may also include a distance sensor. The distance sensor generates an output signal that is indicative of the distance between the femoral and tibial paddles.

The apparatus may further include one or more controllers that determine a joint force value based on the output signal of the force sensor and a distance value based on the output signal of the distance sensor. The apparatus may also include a user interface and may display the force value and/or distance value to a user of the apparatus on the user interface via a display. The display may be a digital display, a series of LEDs, or the like. The apparatus may include actuators coupled to the paddles. The user may control the movement of the paddles by selecting an appropriate button from the user interface. In response, the controller controls the actuator to move the paddles. The apparatus may also transmit the force values and/or distance values to a computer assisted orthopaedic surgery system. In addition, the computer assisted orthopaedic surgery system may control functions of the apparatus by transmitting control and/or data signals to the controllers of the apparatus.

According to another aspect, a method for using a ligament balancer is disclosed. The method may include inserting the ligament balancer between a distal femur and a proximal tibia of the patient. The method may also include moving at least one of a femoral paddle and a tibia paddle away from the other paddle and generating an output signal that is indicative of a force applied to one of the paddles. The method may also include generating an output signal indicative of a distance between the paddles. The output signals and/or values derived therefrom may be transmitted to a computer assisted orthopaedic surgery system.

The above and other features of the present disclosure, which alone or in any combination may comprise patentable subject matter, will become apparent from the following description and the attached drawings.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Figure 1:
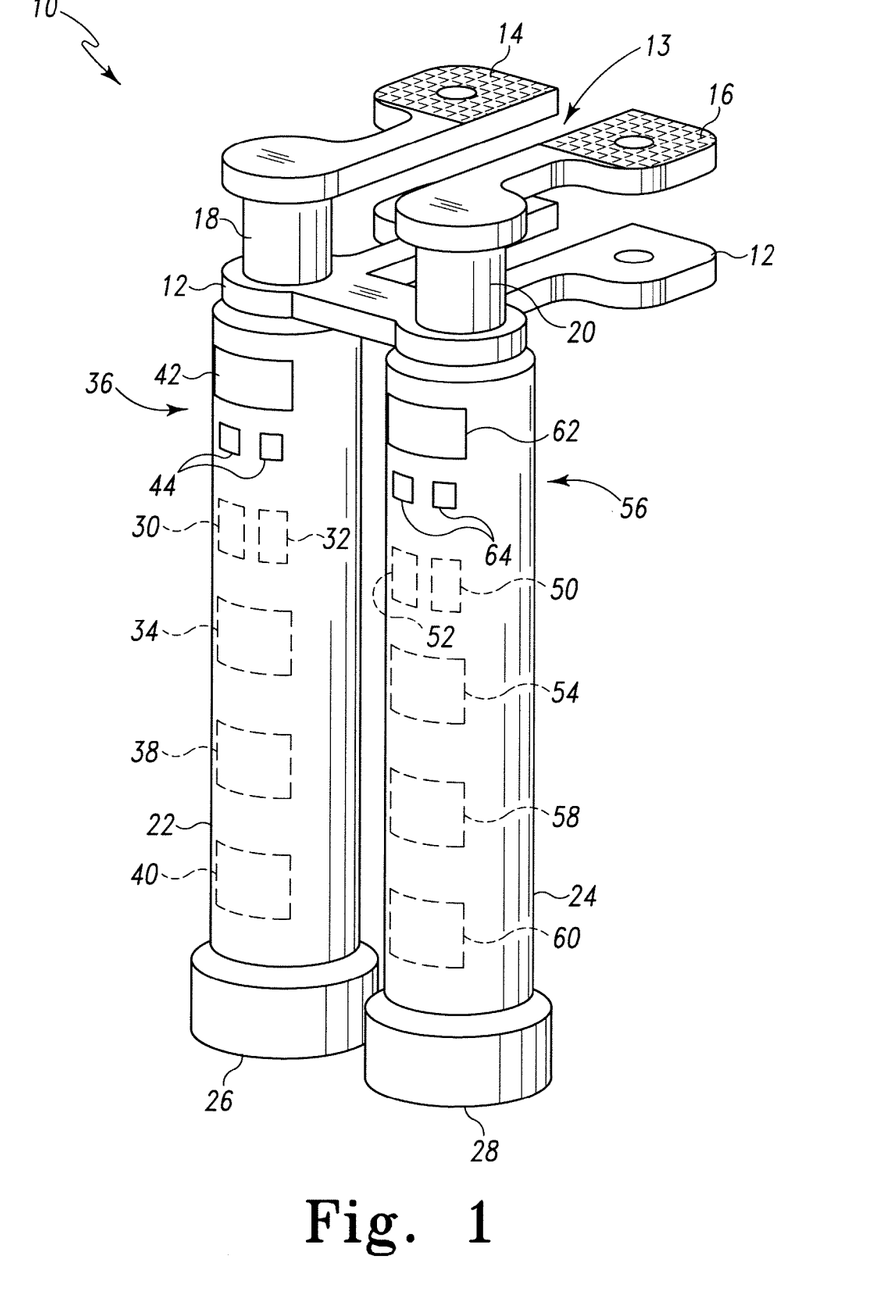
FIG. 1 is a perspective view of an electronic ligament balancer.

Referring to FIG. 1, a ligament balancer 10 for use in an orthopaedic surgical procedure includes a tibial paddle 12, a first femoral paddle 14, and a second femoral paddle 16. The femoral paddle 14 is positioned vertically over and movable away from the tibial paddle 12. Similarly, the femoral paddle 16 is positioned vertically over and movable away from the tibial paddle 12. The tibial paddle 12 is configured to contact a proximal tibia of the patient. As used herein, the term "proximal tibia" is intended to refer to the natural or prosthetic proximal end of a patient's tibia. The tibial paddle 12 may include a mounting slot or aperture 13 configured to receive additional instrumentation such as a flexion adapter, a Ranawat block, and/or an anterior/posterior resection guide.

The femoral paddles 14, 16 are configured to contact a distal femur of the patient. As used herein, the term "distal femur" is intended to refer to the natural or prosthetic distal end of the patient's femur. In use, one of the femoral paddles 14, 16 contacts the medial side of the patient's femur and the other femoral paddle 14, 16 contacts the lateral side of the patient's femur depending on which femur-tibia joint of the patient is being operated on. For the following description, it will be assumed that the ligament balancer 10 is being used on a patient's left knee. Accordingly, femoral paddle 14 and components associated therewith may be described hereinafter as medial femoral paddle 14 and components. Similarly, the femoral paddle 16 and components associated therewith may be described hereinafter as lateral femoral paddle 16 and components.

Figure 2:
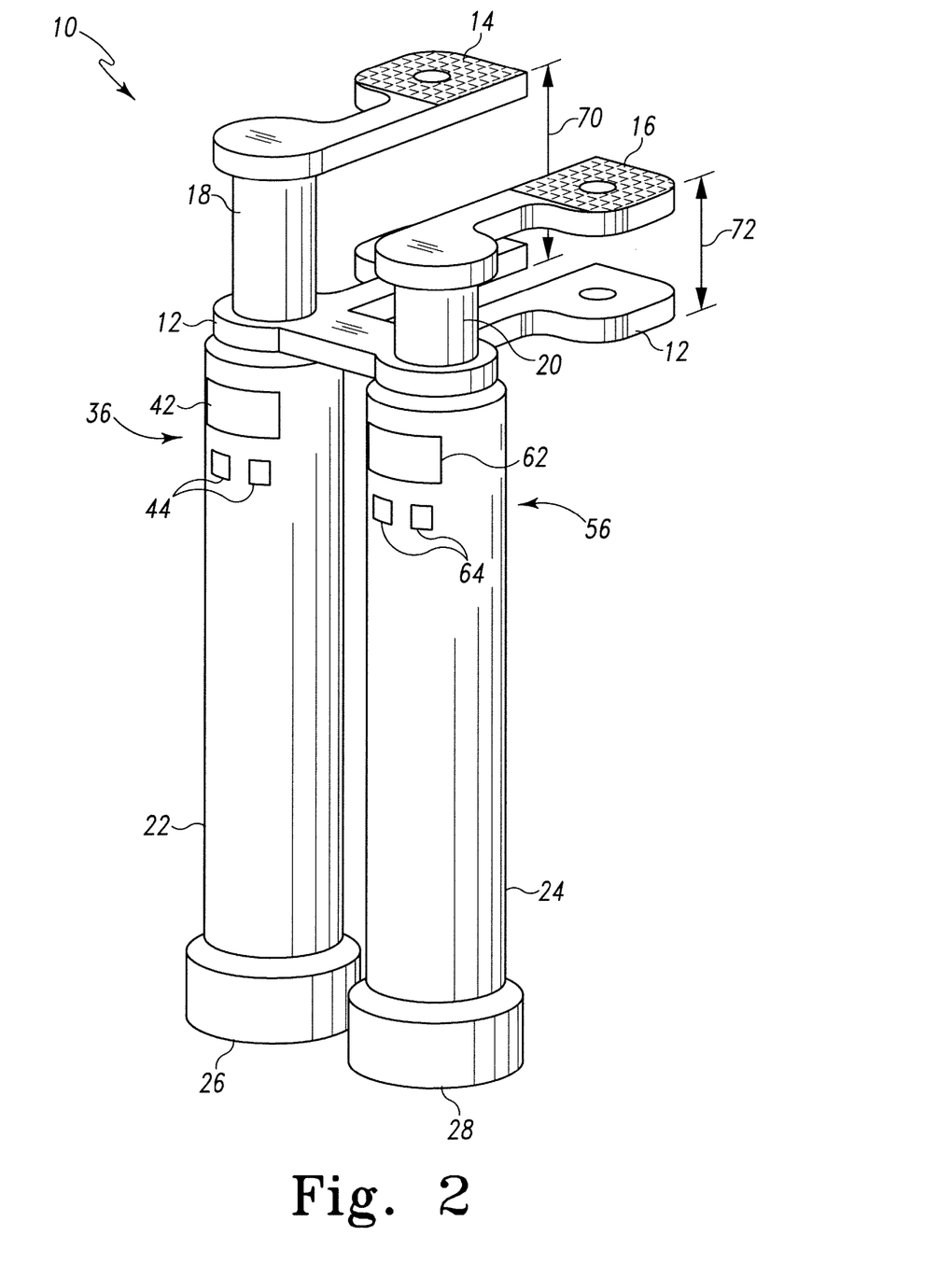
FIG. 2 is another perspective view of the ligament balancer of FIG. 1, note that the femoral paddles are positioned in different positions in FIG. 2.

Each of the femoral paddles 14, 16 is coupled to respective cylinders 18, 20. The cylinders 18, 20 are extendable out of and retractable into respective housings 22, 24. In the illustrative example, the housings 22, 24 are secured to each other via the tibial paddle 12. The medial femoral paddle 14 may be moved away from or toward the tibia paddle 12 by extending or retracting the cylinder 18. The lateral femoral paddle 16 may be moved away from or toward the tibia paddle 12 by extending or retracting the cylinder 20. It should be appreciated that each femoral paddle 14, 16 is independently movable. For example, as illustrated in FIG. 2, the medial femoral paddle 14 may be moved away from the tibial paddle 12 to a distance 70 that is greater than a distance 72 that the lateral femoral paddle 16 is moved away from the tibial paddle 12. Although the femoral paddles 14, 16 are described herein as movable relative to the tibial paddle 12, it should be appreciated that in other embodiments the tibial paddle 12 may be movable rather than or in addition to the femoral paddles 14, 16.

Movement of the femoral paddles 14, 16 may be performed via manual or automated means. For example, in some embodiments, the ligament balancer 10 includes knobs 26, 28 operatively coupled, such as by a screw mechanism, to the cylinders 18, 20, respectively. By manually turning one or both knobs 26, 28 in a clockwise or counterclockwise direction, the cylinders 18, 20 may be extended from or retracted into the respective housings 22, 24 so as to move the femoral paddles 14, 16. In other embodiments, additional or alternative devices for manually moving the femoral paddles 14, 16 away from the tibial paddle 12 may be included. As will be described below in greater detail, in yet other embodiments, such manual adjustment of the ligament balancer may be replaced or included with automated mechanisms.

The ligament balancer 10 includes a force sensor 30, a distance sensor 32, and an actuator 34 positioned in the housing 22. The ligament balancer 10 also includes a force sensor 50, a distance sensor 52, and an actuator 54 positioned in the housing 24. The force sensor 30 is operatively coupled to the cylinder 18 and generates an output signal, such as a voltage signal, indicative of a magnitude of force applied to the medial femoral paddle 14. The force sensor 50 is operatively coupled to the cylinder 20 and generates an output signal, such as a voltage signal, indicative of a magnitude of force applied to the lateral femoral paddle 16. In one particular embodiment, the force sensors 30, 50 are embodied as a load cells, such as miniature load cells.

The distance sensor 32 generates an output signal indicative of a medial distance 70 (see FIG. 2) between the medial femoral paddle 14 and the tibial paddle 12. The distance sensor 52 generates an output signal indicative of a lateral distance 72 (see FIG. 2) between the lateral femoral paddle 16 and the tibial paddle 12. In some embodiments, the distance sensors 32, 52 are electrical devices and generate electrical output signals indicative of the distances 70, 72, respectively. In other embodiments, the distance sensors 32, 52 may be replaced with mechanical distance indicators that create visual signals indicative of the distances 70, 72. For example, the distance sensors 32, 52 may be replaced with indicator needles or other visual indicators coupled to the cylinders 18, 20, and each housing 22, 24 may include a distance scale associated with each needle from which the medial and lateral joint gap distances may be obtained based on the position of the respective needle.

The actuator 34 is operatively coupled to the cylinder 18 and is operable to extend or retract the cylinder 18 in response to a corresponding control signal. Similarly, the actuator 54 is operatively coupled to the cylinder 20 and is operable to extend or retract the cylinder 20 in response to a corresponding control signal. In one particular embodiment, the actuators 34, 54, are embodied as stepper motors. In another embodiment, the actuators 34, 54 are embodied as linear actuators. However, the actuators 34, 54 may be embodied as any prime mover devices operable to extend or retract the cylinders 18, 20. Although the illustrative ligament balancer 10 includes the force sensors 30, 50, the distance sensors 32, 52, and the actuators, 34, 54, in some embodiments, the ligament balancer 10 may include only the force sensors 30, 50, only the distance sensors 32, 52, only the actuators, 34, 54, or any combination thereof.

The ligament balancer 10 illustrated in FIGS. 1 and 2 also includes a user interface 36, a controller 38, and a power supply 40 positioned on or in the housing 22. The ligament balancer 10 also includes a user interface 56, a controller 58, and a power supply 60 positioned on or in the housing 24. The user interface 36 may include a display screen 42 and a number of user buttons 44. Similarly, the user interface 56 may include a display screen 62 and a number of user buttons 64. In other embodiments, however, the display screens 42, 62 may be replaced with a series of light-emitting-diodes (LEDs) or a collection of visual indicators to provide simplified visual feedback to the user of the ligament balancer 10. Additionally, in some embodiments, the user interfaces 36, 56 may be replaced by a remote user interface(s) such as a user interface module that is separate from the housings 22, 24. In such an embodiment, the remote user interface(s) may communicate with the controllers 38, 58 via wired or wireless communication.

The controllers 38, 58 may be embodied as any type of controllers including, for example, general purpose microcontrollers, microprocessors, or application specific integrated circuits (ASICs). The power supplies 40, 60 may be embodied as any devices capable of supplying power to the other respective components such as controllers 38, 58, respectively. In one particular embodiment, the power supplies 40, 60 are embodied as replaceable batteries. In another embodiment, the power supplies 40, 60 are embodied as rechargeable battery packs. In such embodiments, the ligament balancer 10 may include appropriate charging contacts to allow the recharging of the battery packs. Although in the embodiment illustrated in FIG. 1, the ligament balancer 10 includes two user interfaces, two controllers, and two power supplies, it should be appreciated that in other embodiments the ligament balancer 10 may include only one user interface, one controller, and/or one power supply. For example, the ligament balancer 10 may include a single controller positioned in one of the housings 22, 24 and communicatively coupled to each of the force sensors 30, 50, the distance sensors 32, 52, and the actuators 34, 54. Similarly, the ligament balancer 10 may include a single user interface that is communicatively coupled to each of the controllers 38, 58 (or to a single controller).

Figure 3:
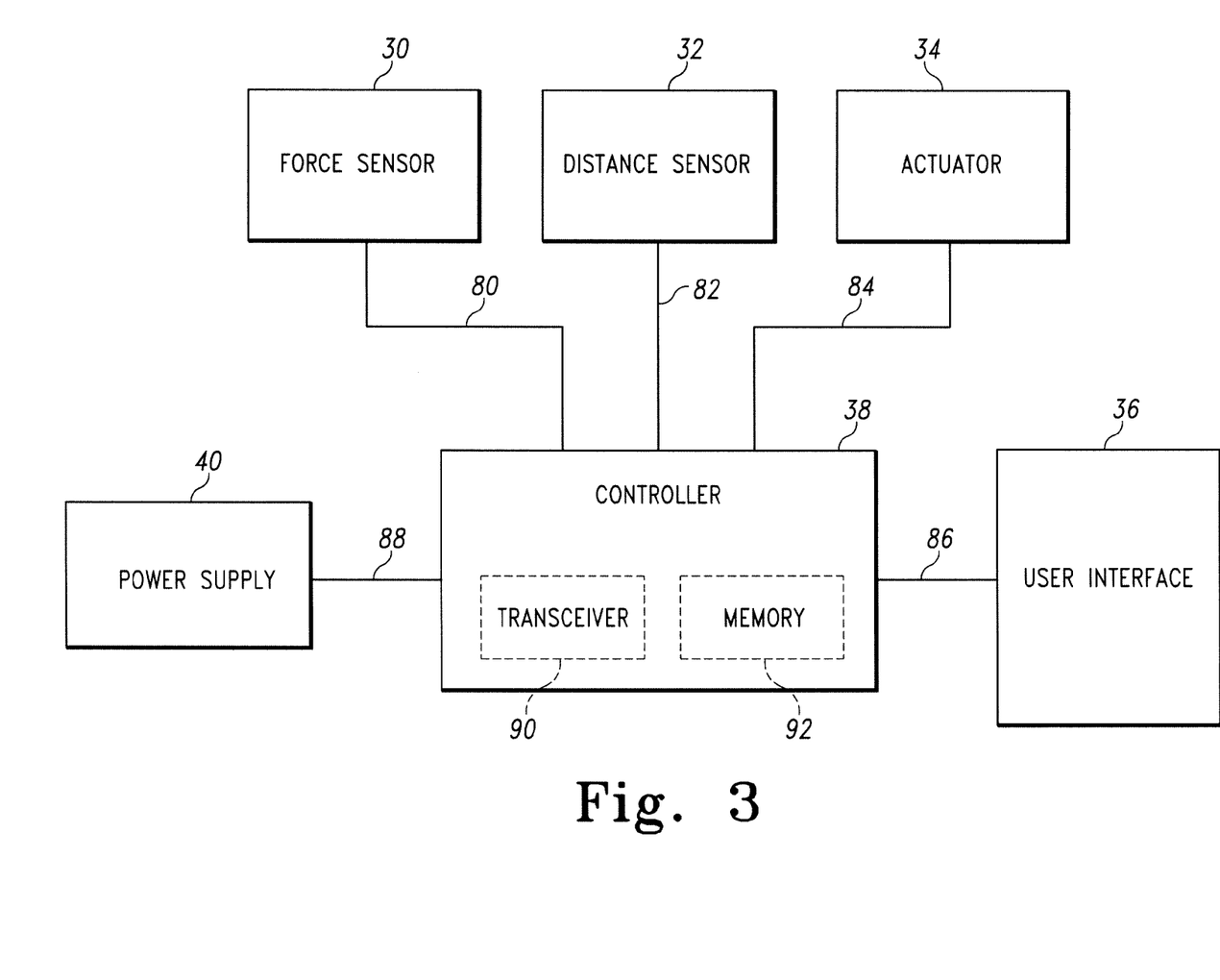
FIG. 3 is a simplified block diagram of an electrical system of the ligament balancer of FIG. 1.

Referring now to FIG. 3, the interconnection of the components included in the medial housing 22 will be described below with the understanding that such description is also applicable to the components included in the lateral housing 24. In addition, it should be further understood that in some embodiments of the ligament balancer 10 only one controller, one user interface, and/or one power supply may be included. Again, the following description is applicable to such embodiments as well.

The controller 38 is communicatively coupled to the force sensor 30, the distance sensor 32, and the actuator 34 via a number of interconnects 80, 82, and 84, respectively. The interconnects 80, 82, 84 may be any type of interconnect capable of enabling communication between the sensor 30, the sensor 32, the actuator 34 and the controller 38 such as wires, printed-circuit-board (PCB) traces, wireless connections, and the like. In addition, the controller 38 is communicatively coupled to the user interface 36 via interconnects 86 and to the power supply 40 via interconnects 88. The controller 38 may further include a receiver, transmitter, or transceiver 90 and a memory device 92 such as a random access memory (RAM) device.

The controller 38 is configured with the appropriate hardware, software, and/or firmware to be responsive to the user commands received via the user interface 36. As such, a surgeon may interact with the ligament balancer 10 via the user interface 36 to control functions of the ligament balancer 10. For example, by use of one of the buttons 44 of the user interface 36, the surgeon can control the actuator 34 to move the medial femoral paddle 14 relative to the tibial paddle 12. In addition or alternatively to the user interface 36, in some embodiments, the surgeon may control the functions of the ligament balancer 10 (e.g., moving the femoral paddle 14) via voice commands In such embodiments, the ligament balancer 10 may include a microphone or other device for receiving voice commands from the surgeon. To facilitate such a feature, the controller 38 may include voice recognition software or devices to facilitate voice control of the ligament balancer 10.

In addition, the controller 38 receives measurement data from the force sensor 30 and the distance sensor 32 via the interconnects 80, 82, respectively. The controller 38 may display the measurement data to the user via the user interface 36 and/or store the measurement data in the memory device 92 for later use. For example, while a patient's leg is positioned in extension, a surgeon may move the medial femoral paddle 14 away from the tibia paddle 12 until a predetermined medial joint force value is achieved as indicated by the force sensor 30 and displayed to the surgeon via the user interface 36. The surgeon may then select one of the buttons 44 to cause the controller 38 to store the medial joint force value and/or the medial joint gap distance, as indicated by the output signal of the distance sensor 32, in the memory device 92. The surgeon may then position the patient's leg in flexion, reinsert the ligament balancer 10, and select another one of the buttons 44 to cause the actuator 34 to move the medial femoral paddle 14 to a position having the same medial joint force as the stored medial joint force value. In this respect, actuation of the femoral paddles 14, 16 may be automated or semi-automated without direct control of the actuators 34, 54 by the user.

Figure 4:
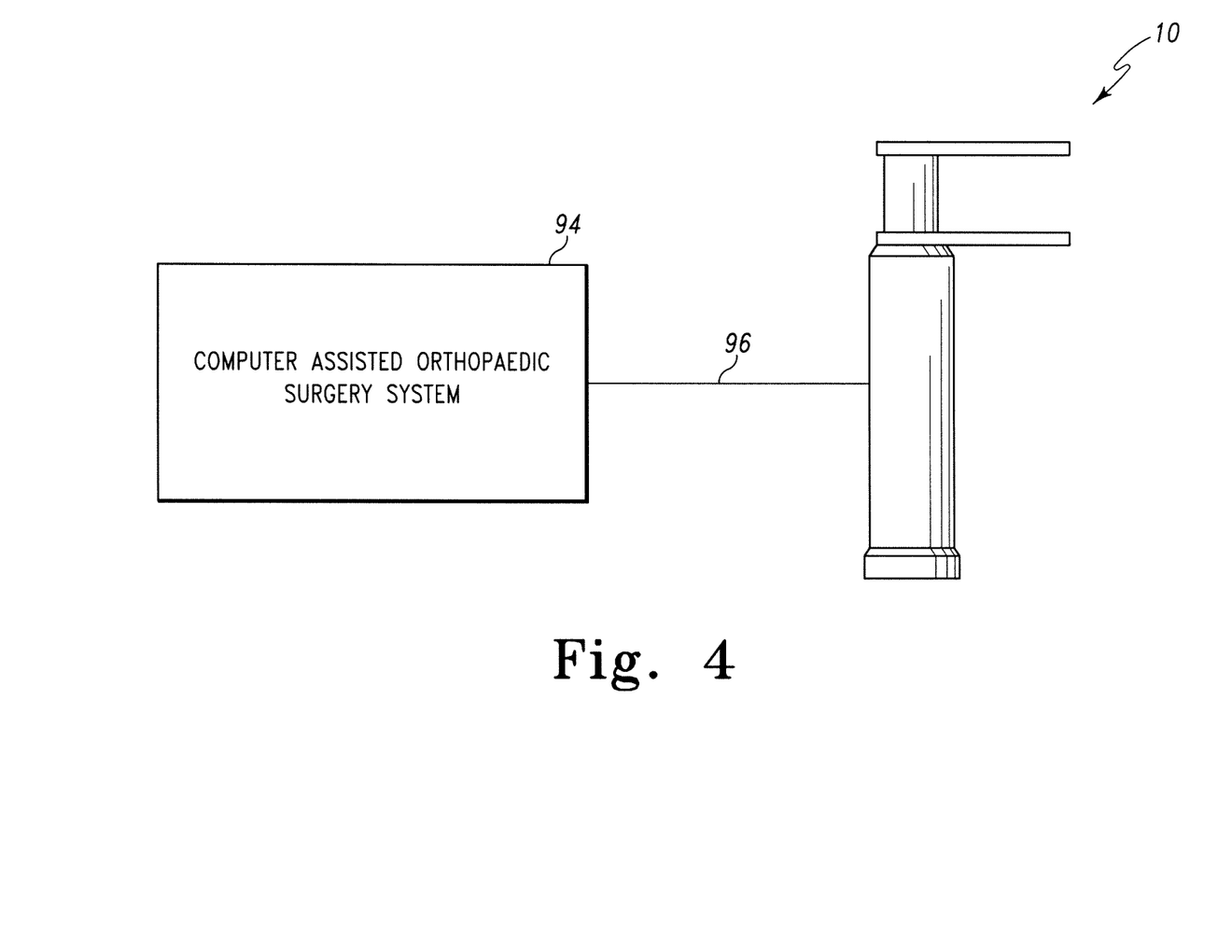
FIG. 4 is a simplified block diagram of a computer assisted orthopaedic surgery system communicatively coupled to the ligament balancer of FIG. 1.

Referring now to FIG. 4, the controller 38 of the ligament balancer apparatus 10 may be configured to communicate with an external controller, computer, or system such as a computer assisted orthopaedic surgery (CAOS) system 94 by use of the transceiver 90 (either wired or wirelessly). In one particular embodiment, the CAOS system 94 is embodied as a Ci™ system commercially available from Depuy Orthopaedics, Inc. of Warsaw, Ind. The controller 38 may communicate with the CAOS system 94 via a communication link 96. The communication link 96 may be any type of communication link including a wired or wireless communication link and may use any type of suitable communication technology and/or protocol including, but not limited to, Ethernet, USB, TCP/IP, Bluetooth, ZigBee, Wi-Fi, Wireless USB, and the like. One communication network that may be used as the communication link 96 to enable wireless communication between the controller 38 and the CAOS system 94 is described in currently pending and commonly owned U.S. patent application Ser. No. 11/024,905 entitled "Medical Device Communications Network", which was filed on Dec. 29, 2004, the entirety of which is expressly incorporated herein by reference.

In some embodiments, the controller 38 transmits measurement data received from the force sensor 30 and/or the distance sensor 32 to the CAOS system 94. The CAOS system 94 may then display the measurement data to the surgeon via a display device (not shown) such as a monitor or the like included in the CAOS system 94 to give the surgeon visual feedback as the surgeon is operating the ligament balancer 10. The CAOS system 94 may also use the measurement data in various calculations or algorithms to determine, for example, surgical suggestions, anatomical simulations resulting from a proposed surgical procedure or step, and the like.

In addition, the CAOS system 74 may communicate with the ligament balancer 10 to control functions of the ligament balancer 10. For example, while a patient's leg is in positioned in extension, a surgeon may move the medial femoral paddle 14 and the lateral femoral paddle 16 away from the tibia paddle 12 until a predetermined medial and lateral joint force value is achieved as indicated by the force sensors 30, 50, respectively. The surgeon may then select one of the buttons 44 and/or one of the buttons 64 to transmit the medial/lateral joint force values and/or the medial/lateral joint gap distances to the CAOS system 94. The CAOS system 94 stores the values for later use. The surgeon may then position the patient's leg in flexion, reinsert the ligament balancer 10, and interact with the CAOS system 94 (e.g., by selecting a button on the CAOS system 94, providing a verbal command to the CAOS system 94, or the like) to cause the CAOS system 94 to transmit control signals including the stored medial/lateral joint force values and/or the stored medial/lateral joint gap distances to the ligament balancer 10. In response, the controller 38 controls the actuator 34 to move the medial femoral paddle 14 to a position having the same medial joint force as the medial joint force value received from the CAOS system 94. Similarly, the controller 58 controls the actuator 54 to move the lateral femoral paddle 16 to a position having the same lateral joint force as the lateral joint force value received from the CAOS system 94. Accordingly, the system 94 may control the functions of the ligament balancer 10 while providing the surgeon with visual feedback data during the surgical procedure.

The ligament balancer 10 may be used to assist a surgeon in balancing ligaments of a knee of a patient. To do so, the patient's knee is positioned in extension (i.e., the patient's tibia is positioned at about 0 degrees relative to the patient's femur). The ligament balancer 10 is then inserted between the patient's distal femur and proximal tibia. Depending upon the surgical procedure being performed and/or the surgeon's general surgical practice, the ligament balancer 10 may be inserted prior to any resection of the bones of the knee, after resection, after knee replacement trials have been positioned on the respective bones, or after the permanent prosthetic knee replacement components have been implanted in the patient. Regardless, the ligament balancer 10 is positioned between the patient's femur and tibia such that the femoral paddles 14, 16 contact the natural or prosthetic distal femur and the tibial paddle 12 contacts the natural or prosthetic proximal tibial.

Once the ligament balancer is properly positioned, the surgeon may move the femoral paddles 14, 16 away from the tibial paddle 12 until a predetermined medial and lateral joint force is achieved. This may be accomplished manually by turning the knobs 26, 28 until the desired joint force value is achieved. Alternatively, this may be accomplished by selecting one of the buttons 44, 64 of the user interfaces 36, 56 to cause the actuators 34, 54 to move the femoral paddles 14, 16 until the desired joint force value is achieved. In some embodiments, this may also be accomplished by supplying the CAOS system 94 with the desired joint force value. In response, the CAOS system 94 transmits the appropriate control signals to the ligament balancer 10 to cause the actuators 34, 54 to move the femoral paddles 14, 16 away from the tibial paddle 12 until the desired joint force value is achieved.

Each of the femoral paddles 14, 16 may be moved separately and independently of each other. Because of irregularities in the patient's anatomy, the femoral paddles 14, 16 may need to be moved to different distances to achieve the same desired joint force value. If so, the extension gap (i.e., the gap between the distal femur and the proximal tibia when the knee is in extension) will not have a rectangular shape. Because a generally rectangular shaped extension gap is desirable, the surgeon may perform ligament release on one or more ligaments to allow the femoral paddles 14, 16 to be equally positioned while maintaining the desired joint force value.

It should be understood that as the surgeon is moving the femoral paddles 14, 16, the medial and lateral joint forces (i.e., the forces being applied to each paddle 14, 16) are determined by the force sensors 30, 50, respectively. The controller 38 calculates a force value based on the output signal of the force sensor 30 and displays the force value to the surgeon via the display 42 of the user interface 36. Similarly, the controller 58 calculates a force value based on the output signal of the force sensor 50 and displays the force value to the surgeon via the display 62 of the user interface 56. The force values displayed on the user interfaces 36, 56 may be numerical values or may be represented by a number of LEDs. In some embodiments, the distance 70 which the medial femoral paddles 14 is moved away from the tibial paddle 12 is determined by the distance sensor 32 and also displayed to the surgeon via the user interface 36. Similarly, the distance 72 which the lateral femoral paddles 16 is moved away from the tibial paddle 12 is determined by the distance sensor 52 and also displayed to the surgeon via the user interface 56. Further, in some embodiments, the force values and/or distance values may be transmitted to the CAOS system 94. The CAOS system 94 may display the force and/or distance values to the surgeon to provide a visual feedback to the surgeon as the surgeon is manipulating the femoral paddles 14, 16. Further, the CAOS system 94 may have additional sensors or devices to determine when the desirable rectangular shaped extension gap is achieved and alert the user to such (e.g., by an audible or visual alert).

In addition to displaying the force values and distance values to the surgeon, the controllers 38, 58 may store the values for later use. For example, once the surgeon has moved the medial femoral paddle 14 to achieve the desired medial joint force value, the surgeon may select one of the buttons 44 to cause the controller 38 to store the medial joint force value and, in some embodiments, the distance 70 at which the medial femoral paddle 14 is moved away from the tibial paddle 12. Similarly, once the surgeon has moved the lateral femoral paddle 16 to achieve the desired lateral joint force value, the surgeon may select one of the buttons 64 to cause the controller 58 to store the lateral joint force value and, in some embodiments, the distance 72 at which the lateral femoral paddle 16 is moved away from the tibial paddle 12. In addition or alternatively, the CAOS system 94 may store the joint force values and/or distance values for later use.

After the surgeon has achieved the desired extension gap and performed any necessary ligament release, the femoral paddles 14, 16 are moved toward the tibial paddle 12 so that the ligament balancer 10 may be removed from the patient's knee joint. The patient's knee is then positioned in flexion (i.e., the patient's tibia is positioned at about 90 degrees relative to the patient's femur) and the ligament balancer 10 is reinserted between the patient's distal femur and proximal tibia. The femoral paddles 14, 16 are again moved away from the tibia paddle 12 until the desired medial and lateral joint force values are achieved. To do so, the surgeon may select one of the buttons 44 of the user interface 36 to move the medial femoral paddle 14 away from the tibial paddle 12 until the desired medial joint force value, as determined by the force sensor 30, is achieved. Similarly, the surgeon may select one of the buttons 64 of the user interface 56 to move the lateral femoral paddle 16 away from the tibial paddle 12 until the desired lateral joint force value, as determined by the force sensor 50, is achieved. Typically, it is desirable to use the same force value for both the flexion joint force and the extension joint force.

In another embodiment, the surgeon may select another one of the buttons 44 to cause the controller 38 to retrieve the stored medial joint force value from memory. The controller 38 then controls the actuator 34 to move the medial femoral paddle 14 away from the tibial paddle 12 until the medial joint force, as measured by the joint force sensor 30, equals the retrieved medial joint force value. Similarly, the surgeon may select another one of the buttons 64 to cause the controller 58 to retrieve the stored lateral joint force value from memory. The controller 58 then controls the actuator 54 to move the lateral femoral paddle 16 away from the tibial paddle 12 until the lateral joint force, as measured by the joint force sensor 50, equals the retrieved lateral joint force value.

In yet another embodiment, the CAOS system 94 controls the movement of the femoral paddles 14, 16 by transmitting control signals to the respective controllers, 38, 58. For example, after the ligament balancer 10 has been reinserted into the knee area of the patient, the surgeon may press another button on the user interface 36 and/or on the user interface 56 to cause the controllers 38, 58 to send a ready signal to the CAOS system 94 informing the CAOS system 94 that the ligament balancer 10 is ready to receive control signals. In response to the ready signal, the CAOS system 94 retrieves the stored medial and lateral joint force values from memory and transmits the retrieved values to the respective controllers 38, 58. The controller 38 then controls the actuator 34 to move the medial femoral paddle 14 away from the tibial paddle 12 until the medial joint force, as measured by the joint force sensor 30, equals the received medial joint force value. The controller 58 controls the actuator 54 to move the lateral femoral paddle 16 away from the tibial paddle 12 until the lateral joint force, as measured by the joint force sensor 50, equals the received lateral joint force value.

In yet a further embodiment, the surgeon may control the movement of the femoral paddles 14, 16 via the CAOS system 94 rather than the respective user interfaces 36, 56. For example, the user may enter in a desired joint force value into the CAOS system 94. In response, the CAOS system 94 communicates the entered joint force value to the ligament balancer 10 to cause the movement of the femoral paddles 14, 16 until the desired joint force value is achieved.

Once the femoral paddles 14, 16 have been moved to the appropriate positions to achieve the desired joint force values, the surgeon may, if desirable, perform any necessary ligament release, as described above, to develop a more rectangular shaped flexion gap. After the ligament release is preformed, the femoral paddles 14, 16 are moved toward the tibial paddle 12 and the ligament balancer 10 is removed from the knee area of the patient.

Although the ligament balancer 10 has been described herein in reference to a knee joint of a patient, it should be understood that the ligament balancer 10 may be used on other joints of the patient. For example, the ligament balancer 10 may be used on an elbow joint of the patient. As such, it should be appreciated that although some of the components have been described in reference to certain bones of the patient (e.g., femoral and tibial paddles), such components would be configured to be used on or with the appropriate bones of the patient's joint being operated on.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatuses, systems, and methods described herein. It will be noted that alternative embodiments of the apparatuses, systems, and methods of the present disclosure may not include all of the features described yet still benefit from at least some of the advantages of such features. Those of ordinary skill in the art may readily devise their own implementations of the systems and methods that incorporate one or more of the features of the present invention and fall within the spirit and scope of the present disclosure as defined by the appended claims.

The invention claimed is:

1. An orthopaedic surgical instrument comprising:
   an orthopaedic distraction device comprising:
   an upper surface shaped to contact a distal end of a patient's femur,
   a lower surface configured to contact a proximal end of the patient's tibia, and
   a spacing mechanism including an actuator positioned in the orthopaedic distraction device that is operable to move the upper surface relative to the lower surface,
   a user-operated control device secured to the orthopaedic distraction device and including a button positioned on the outer surface of the orthopaedic distraction device, wherein the user-operated control device is operable to actuate the spacing mechanism to move the upper surface relative to the lower surface in response to a user pressing the button,
   a display positioned on an outer surface of the orthopaedic distraction device and configured to provide visual feedback indicative of a force between the patient's tibia and the patient's femur, and
   a circuit positioned in the orthopaedic distraction device and configured to control the display.

2. The orthopaedic surgical instrument of claim 1, wherein the user-operated control device includes a body configured to rotate to actuate the spacing mechanism to move the upper surface relative to the lower surface.

3. The orthopaedic surgical instrument of claim 1, wherein the upper surface has a medial section shaped to engage a medial condyle of the patient's femur and lateral section shaped to engage a lateral condyle of the patient's femur.

4. The orthopaedic surgical instrument of claim 3, further comprising a second display positioned on the outer surface of the orthopaedic distraction device, wherein (i) the display is a first display configured to provide visual feedback indicative of a first force between the patient's tibia and a lateral portion of the patient's femur, and (ii) the second display is configured to provide visual feedback indicative of a second force between the patient's tibia and a medial portion of the patient's femur.

5. The orthopaedic surgical instrument of claim 3, further comprising a plurality of pressure sensors, the plurality of pressure sensors including (i) a first pressure sensor configured to generate a first electrical signal indicative of a lateral force on the lateral section, and (ii) a second pressure sensor configured to generate a second electrical signal indicative of a medial force on the medial section.

6. The orthopaedic surgical instrument of claim 3, further comprising a plurality of distance sensors, the plurality of distance sensors including (i) a first distance sensor configured to generate a first electrical signal indicative of a lateral distance between the lateral section of the upper surface and the lower surface, and (ii) a second distance sensor configured to generate a second electrical signal indicative of a medial distance between the medial section of the upper surface and the lower surface.

7. The orthopaedic surgical instrument of claim 3, wherein the orthopaedic distraction device comprises a first femoral paddle that includes the medial section and a second femoral paddle that includes the lateral section.

8. The orthopaedic surgical instrument of claim 7, wherein the orthopaedic distraction device includes a tibial paddle including the lower surface.

9. The orthopaedic surgical instrument of claim 7, wherein the first femoral paddle and the second femoral paddle are configured to move independently.

10. The orthopaedic surgical instrument of claim 1, wherein the circuit includes a memory device operable to store a digital representation of the force between the patient's tibia and the patient's femur.

11. The orthopaedic surgical instrument of claim 10, wherein the button is a first button, and the orthopaedic surgical instrument further comprises a second button positioned on the outer surface of the orthopaedic distraction device that is configured to generate an electrical signal when pressed, wherein the memory device is configured to store the digital representation of the force in response to receiving the electrical signal.

12. An orthopaedic surgical instrument comprising:
    an orthopaedic distraction device comprising:
    an upper body having a medial surface to contact a medial section of a distal end of a patient's femur and a lateral surface to contact a lateral section of the distal end of the patient's femur,
    a lower body including a second surface configured to contact a proximal end of the patient's tibia, and
    a spacing mechanism coupled to the upper body and including an actuator that is operable to move the upper body relative to the lower body, a user-operated control device secured to the lower body and including a button positioned on an outer surface of the lower body, wherein the user-operated control device is operable to actuate the spacing mechanism to move the upper body in response to a user pressing the button, a display positioned on an outer surface of the orthopaedic distraction device and configured to provide visual feedback indicative of a force between the patient's tibia and the patient's femur, and a circuit positioned in the lower body and configured to control the display.

13. The orthopaedic surgical instrument of claim 12, wherein the orthopaedic distraction device comprises a first femoral paddle that includes the medial section and a second femoral paddle that includes the lateral section.

14. An orthopaedic surgical instrument comprising:

an orthopaedic distraction device sized to be positioned between a distal end of a patient's femur and a proximal end of the patient's tibia, the orthopaedic distraction device being configured to apply force between the patient's femur and the patient's tibia, a user-operated control device including (i) a rotary input coupled to the orthopaedic distraction device, the rotary input being operable to actuate the orthopaedic distraction device to apply force between the patient's femur and the patient's tibia, and (ii) a button that is positioned on an outer surface of the orthopaedic distraction device, a display positioned on an outer surface of the orthopaedic distraction device and configured to provide visual feedback indicative of force applied by the distraction device, and a circuit positioned in the orthopaedic distraction device and configured to control the display, wherein the orthopaedic distraction device is operable to apply force in response to the electrical signal generated by the button.

* * * * *